US012716083B2

(12) United States Patent
Eyvrard et al.

(10) Patent No.: US 12,716,083 B2
(45) Date of Patent: Aug. 25, 2026

(54) BIOSENSOR COMPRISING A PLURALITY OF FUNCTIONALIZED SETS OF CARBON ATOMS IN THE SP$^2$ HYBRIDISATION STATE, PREPARATION METHOD THEREOF AND USE THEREOF, IN PARTICULAR FOR THE DETECTION OF ECOTOXICOLOGICAL RISKS

(71) Applicant: COMMISSARIAT A L'ENERGIE ATOMIQUE ET AUX ENERGIES ALTERNATIVES, Paris (FR)

(72) Inventors: Doriane Eyvrard, Grenoble (FR); Thomas Alava, Grenoble (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 456 days.

(21) Appl. No.: 18/323,489

(22) Filed: May 25, 2023

(65) Prior Publication Data

US 2024/0011069 A1 Jan. 11, 2024

(51) Int. Cl.

*C12Q 1/04* (2006.01)
*A01N 63/50* (2020.01)
*A01P 1/00* (2006.01)

(52) U.S. Cl.

CPC ............... *C12Q 1/04* (2013.01); *A01N 63/50* (2020.01); *A01P 1/00* (2021.08)

(58) Field of Classification Search

None

See application file for complete search history.

(56) References Cited

U.S. PATENT DOCUMENTS

2011/0136691 A1 6/2011 Kim et al.
2022/0030855 A1 2/2022 Alava et al.

FOREIGN PATENT DOCUMENTS

EP 3944763 A1 2/2022

OTHER PUBLICATIONS

Kumar et al., Simple and versatile non-covalent functionalization protocol turning graphene bacteriophilic, bacteriostatic or bactericidal, abstract for Graphene 2020, Oct. 19-22, 2020, Grenoble France (Year: 2020).*

Mann et al., Preservation of Antibody Selectivity on Graphene by Conjugation to a Tripod Monolayer, Angew. Chem. Int. Ed., 52, 3177-3180, published 2013 (Year: 2013).*

Ngo et al., Quartz crystal microbalance (QCM) as biosensor for the detecting of *Escherichia coli* O157:H7, Adv. Nat. Sci.: Nanosci. Nanotechnol. 5 (2014) 045004 (8pp) (Year: 2014).*

Bitton et al., "Bacterial and Enzymatic Bioassays for Toxicity Testing in the Environment," Reviews of Environmental Contamination and Toxicology, 125 (1992).

La Spina et al., "New Detection Platform for Screening Bacteria in Liquid Samples," Biosensors, 11: 142 (2021).

* cited by examiner

*Primary Examiner* — Anna R Falkowitz
*Assistant Examiner* — Edwin Coleman Mitchell
(74) *Attorney, Agent, or Firm* — Morgan, Lewis & Bockius LLP

(57) ABSTRACT

The present invention relates to a biosensor comprising a plurality of functionalized sets of carbon atoms in the sp$^2$ hybridisation state, its method of preparation and its use, in particular for the detection of ecotoxicological risks, in particular the determination of the toxicity of substances present in an aqueous medium, as well as to the corresponding determination method.

12 Claims, 1 Drawing Sheet

Specification includes a Sequence Listing.

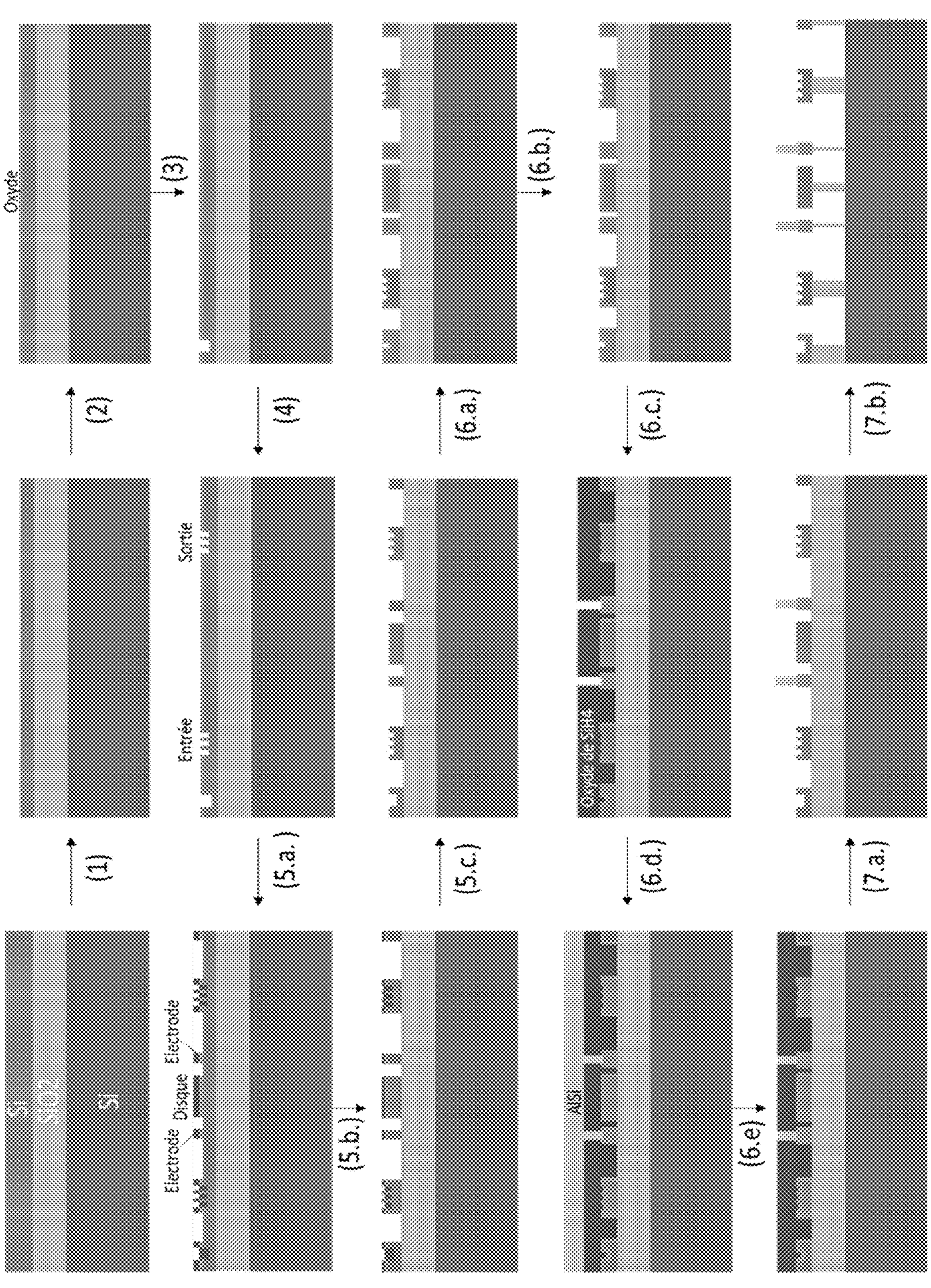
Si
SiO2
Si
Oxyde
Electrode
Disque
Electrode
Entrée
Sortie
(1)
(2)
(3)
(4)
(5.a.)
(5.b.)
(5.c.)
(6.a.)
(6.b.)
(6.c.)
(6.d.)
(6.e)
(7.a.)
(7.b.)

SEQUENCE LISTING

```
Sequence total quantity: 11
SEQ ID NO: 1            moltype = AA  length = 37
FEATURE                 Location/Qualifiers
source                  1..37
                        mol_type = protein
                        organism = Hyalophora cecropia
SEQUENCE: 1
KWKLFKKIEK VGQNIRDGII KAGPAVAVVG QATQIAK                           37

SEQ ID NO: 2            moltype = AA  length = 35
FEATURE                 Location/Qualifiers
source                  1..35
                        mol_type = protein
                        organism = Hyalophora cecropia
SEQUENCE: 2
KWKVFKKIEK MGRNIRNGIV KAGPAIAVLG EAKAL                             35

SEQ ID NO: 3            moltype = AA  length = 31
FEATURE                 Location/Qualifiers
source                  1..31
                        mol_type = protein
                        organism = Hyalophora cecropia
SEQUENCE: 3
SWLSKTAKKL ENSAKKRISE GIAIAIQGGP R                                 31

SEQ ID NO: 4            moltype = AA  length = 63
FEATURE                 Location/Qualifiers
source                  1..63
                        mol_type = protein
                        organism = Ceratitis capitata
SEQUENCE: 4
MNFNKVFILV AIVIAIFAGQ TEAGWLKKIG KKIERVGQHT RDATIQTIAV AQQAANVAAT  60
ARG                                                                63

SEQ ID NO: 5            moltype = AA  length = 35
FEATURE                 Location/Qualifiers
source                  1..35
                        mol_type = protein
                        organism = Bombyx mori
SEQUENCE: 5
RWKIFKKIEK VGQNIRDGIV KAGPAVAVVG QAATI                             35

SEQ ID NO: 6            moltype = AA  length = 100
FEATURE                 Location/Qualifiers
source                  1..100
                        mol_type = protein
                        organism = Homo sapiens
SEQUENCE: 6
MRTLTILTAV LLVALQAKAE PLQAEDDPLQ AKAYEADAQE QRGANDQDFA VSFAEDASSS  60
LRALGSTRAF TCHCRRSCYS TEYSYGTCTV MGINHRFCCL                        100

SEQ ID NO: 7            moltype = AA  length = 94
FEATURE                 Location/Qualifiers
source                  1..94
                        mol_type = protein
                        organism = Homo sapiens
SEQUENCE: 7
MRTIAILAAI LLVALQAQAE SLQERADEAT TQKQSGEDNQ DLAISFAGNG LSALRTSGSQ  60
ARATCYCRTG RCATRESLSG VCEISGRLYR LCCR                              94

SEQ ID NO: 8            moltype = AA  length = 23
FEATURE                 Location/Qualifiers
source                  1..23
                        mol_type = protein
                        organism = Xenopus borealis
SEQUENCE: 8
GIGKFLHSAG KFGKAFLGEV MKS                                          23

SEQ ID NO: 9            moltype = AA  length = 23
FEATURE                 Location/Qualifiers
source                  1..23
                        mol_type = protein
                        organism = Xenopus ruwenzoriensis
SEQUENCE: 9
GIKEFAHSLG KFGKAFVGGI LNQ                                          23

SEQ ID NO: 10           moltype = AA  length = 70
FEATURE                 Location/Qualifiers
```

-continued

```
source                  1..70
                        mol_type = protein
                        organism = Phyllomedusa hypochondrialis
SEQUENCE: 10
MAFLKKSLFL VLFLGMVSLS ICEEEKRENE DEELQEDDEQ SEMKRGLWST IKNVGKEAAI  60
AAGKAALGAL                                                        70

SEQ ID NO: 11           moltype = AA  length = 79
FEATURE                 Location/Qualifiers
source                  1..79
                        mol_type = protein
                        organism = Phyllomedusa sauvagei
SEQUENCE: 11
MDILKKSLFL VLFLGLVSLS ICEEEKRENE DEEKQEDDEQ SEMKRALWKT MLKKLGTMAL  60
HAGKAALGAA ADTISQGTQ                                              79
```

BIOSENSOR COMPRISING A PLURALITY OF FUNCTIONALIZED SETS OF CARBON ATOMS IN THE $SP^2$ HYBRIDISATION STATE, PREPARATION METHOD THEREOF AND USE THEREOF, IN PARTICULAR FOR THE DETECTION OF ECOTOXICOLOGICAL RISKS

SEQUENCE LISTING SUBMISSION VIA EFS-WEB

The contents of the electronic sequence listing (sequence-listing.xml; Size: 11,306 bytes; and Date of Creation: May 25, 2023) is herein incorporated by reference in its entirety.

The present invention relates to a biosensor comprising a plurality of functionalized sets of carbon atoms in the $sp^2$ hybridisation state, its method of preparation and its use, in particular for the detection of ecotoxicological risks, in particular the determination of the toxicity of substances present in an aqueous medium, as well as to the corresponding determination method.

The potential impacts of the omnipresence of contaminants in the environment due to urbanisation, agriculture and industrial activities on the health of populations is a major public health concern.

A regular analysis must therefore be implemented to monitor the levels of contamination and ecotoxicity, and assessing these impacts is a major challenge for society.

The methodology of the assessment of the ecotoxicological risk was developed in the 1980s as a tool allowing for assessing the impacts of the exposure to the environmental contaminants on the health of populations. This methodology has been used to assess the safety of the products and the impacts of new industrial projects, to establish criteria and standards or to validate certain exposure levels allowed by regulations.

Traditionally, the methodology of the assessment of the risks comprises the following four steps: the identification of the hazard, the definition of the dose-response relationships, the target exposure assessment, and the risk characterisation.

This assessment of the risks is based on laboratory tests carried out on different biological/biochemical models, for different exposure times (short or long, for the assessment of a possible acute or chronic toxicity).

However, these risks are most likely underestimated because the cocktail effect, which can generate greater toxicities than the molecules studied in isolation, is not assessed on a realistic scale. Indeed, the cocktail effect is currently assessed in laboratory by studying the dangerousness of a known set of exogenous molecules, or by applying algorithms to a set of toxic concentrations measured in the laboratory on substances studied separately. In this context, not all the molecules actually present in the natural environment can be considered.

A cocktail effect occurs when a chemical substance, thought to be harmless at low doses, becomes harmful at the same dose, or even at lower doses, if it is present in a mixture with at least one other. Its toxicity is potentiated by the action of the other substance.

Thus, the above-mentioned methodologies do not allow to know what the interactions between several substances are, what the effects are when one is exposed to several substances at the same time. This is generally the case in the natural environment:living organisms and human beings are constantly exposed to many different substances:drugs, pesticides, endocrine disruptors, pollutants, contaminants, volatile organic compounds, the corresponding secondary products and by-products.

To understand all the possible effects of all these substances, it would therefore be necessary to be able to observe their simultaneous effects on an organism.

To this end, methods for the in situ detection of ecotoxic effects induced by pollutants on model aquatic organisms in eco-toxicology have been developed more recently.

These methods concern in particular the analysis of the quality of an aquatic environment with the help of biomonitoring tools using the exposure of gammarid populations to in particular identify the existence or not of an ecotoxicity linked to the presence of pollutants in the environment, its level of intensity and its evolution over time.

However, these methods do not allow for the automation of the acquisition of the results.

In addition, the time required to obtain these results is excessively long, as it involves many time-consuming steps (gammarid rearing, selection, installation on site, recovery and laboratory analysis, etc.).

The purpose of the invention is to allow the implementation of a biosensor for a detection and an assessment of the ecotoxicological risks, for example in the natural environments and the industrial waters, which avoids the aforementioned disadvantages.

Thus, one aim of the invention is to provide an in-situ method for obtaining results quickly, while allowing at the same time saving the space required to obtain these results.

A further aim of the invention is to provide a method allowing for obtaining measured results in real time, by means that can be automated and miniaturised.

Thus, according to a first aspect, the invention relates to a biosensor comprising:

a first set A of carbon atoms in the $sp^2$ hybridisation state, said set being in contact with:

a plurality of compounds of the following formula ($I_1$):

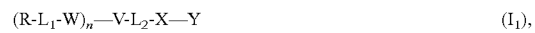

$(R\text{-}L_1\text{-}W)_n\text{—}V\text{-}L_2\text{-}X\text{—}Y \quad (I_1),$ and optionally, a plurality of compounds of the following formula ($II_1$):

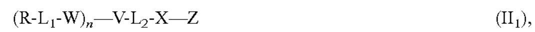

$(R\text{-}L_1\text{-}W)_n\text{—}V\text{-}L_2\text{-}X\text{—}Z \quad (II_1),$ a second set B of carbon atoms in the $sp^2$ hybridisation state, said set being in contact with:

a plurality of compounds of the following formula ($II_2$):

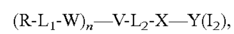

$(R\text{-}L_1\text{-}W)_n\text{—}V\text{-}L_2\text{-}X\text{—}Y(I_2),$ and a plurality of compounds of the following formula ($II_2$):

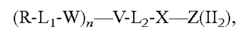

$(R\text{-}L_1\text{-}W)_n\text{—}V\text{-}L_2\text{-}X\text{—}Z(II_2),$ at least one third set C of carbon atoms in the $sp^2$ hybridisation state, said set being in contact with:

a plurality of compounds of the following formula ($I_3$):

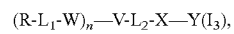

$(R\text{-}L_1\text{-}W)_n\text{—}V\text{-}L_2\text{-}X\text{—}Y(I_3),$ and a plurality of compounds of the following formula ($II_3$):

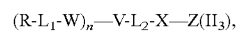

$(R\text{-}L_1\text{-}W)_n\text{—}V\text{-}L_2\text{-}X\text{—}Z(II_3),$ with, independently of the carbon set A to C and of the compound of the formula (I) to (II):

n is equal to 1, 2, or 3, in particular 3;

V represents, for all n, $\text{—}C(H)_{3\text{-}n}\text{—}$ or:

when n is equal to 2, —C(H)═, C being in this case bonded to $L_2$ by a double bond;

when n is equal to 1. —C≡. C being in this case bonded to $L_2$ by a triple bond;

R is an aromatic hydrocarbon comprising from 2 to 6 condensed aromatic cycles;

$L_1$ is a $C_1$-$C_{12}$ alkanediyl group;

W represents a single bond, an arenediyl group, a heteroarenediyl group or a —O—$Ar_1$— group where $Ar_1$ is an arene or a heteroarene;

$L_2$ is a group of formula (A) as follows, $-(L_{2a})_i-(L_{2b})_j-$ wherein:

- i and j are independently of each other selected from 0 and 1, with i+j=1 or 2;
- $L_{2a}$ is a $C_1$-$C_{12}$ alkanediyl, $C_2$-$C_{12}$ alkenediyl or $C_2$-$C_{12}$ alkynediyl group;
- $L_{2b}$ is an arenediyl group, a heteroarenediyl group or a group —O—$Ar_2$— where $Ar_2$ is an arene or a heteroarene;

X is —C(=O)N—, —C(=O)O— or —C(=O)S— group;

Y is an antibacterial antibody or a lectin;

Z is an antibacterial peptide;

and where the sets A, B and C are such that:

- the set A is free of compounds of the formula ($II_1$) or the molar ratio of the amount of compounds of the formula ($II_1$) to that of compounds of the formula ($I_1$) is less than 0.1;
- in the set B, the molar ratio of the amount of compounds of the formula ($I_2$) to that of compounds of the formula ($II_2$) being from 0.66 to 1.5, for example about 1.0; and
- in the set C, the molar ratio of the amount of compounds of the formula ($I_3$) to that of compounds of the formula ($II_3$) being from 0.33 to 0.66, for example about 0.5.

Thus, in both formulae (I) and (II) (i.e., the formulae ($I_1$), ($II_1$), ($I_2$), ($II_2$), ($I_3$), and ($II_3$)), C represents a tetravalent carbon atom in the case where V represents $—C(H)_{3-n}—$ (—C—, —CH—, or —$CH_2$— depending on the value of n); a trivalent carbon atom when V represents —C(H)=; or a divalent carbon atom when V represents —C≡.

By "in contact" is meant in particular that the aromatic hydrocarbons (R) of the compounds of the formulae (I) and (II) form Pi-stacking bonds with the set of carbon atoms in the $sp^2$ hybridisation state. These bonds, also referred to as π-π stacking, are non-covalent bonds, among the strongest of the non-covalent bonds.

According to a particular embodiment, the biosensor according to the invention comprises at least two sets C of carbon atoms in the $sp^2$ hybridisation state, for which the molar ratio of the amount of compounds of the formula ($I_3$) to that of compounds of the formula ($II_3$), being from 0.33 to 0.66, differs.

According to a particular embodiment, the biosensor according to the invention comprises at least two sets B of carbon atoms in the $sp^2$ hybridisation state, for which the molar ratio of the amount of compounds of the formula ($I_2$) to that of compounds of the formula ($II_2$), being from 0.66 to 1.5, differs.

According to a particular embodiment, the biosensor according to the invention comprises at least two sets B of carbon atoms in the $sp^2$ hybridisation state, for which the molar ratio of the amount of compounds of the formula ($I_2$) to that of compounds of the formula ($II_2$) being from 0.66 to 1.5, differs and comprising at least two sets C of carbon atoms in the $sp^2$ hybridisation state, for which the molar ratio of the amount of compounds of the formula ($I_3$) to that of compounds of the formula ($II_3$), being from 0.33 to 0.66, differs.

According to a particular embodiment, said sets A, B and C of carbon atoms in the $sp^2$ hybridisation state are independently selected from graphene, graphene oxide, graphite, carbon nanotubes, fullerenes and fullerites, said sets being in particular graphene, more particularly in the form of sheets or flakes.

By "sheet" is meant notably graphene, in particular single layer, two of whose dimensions are greater than 1 mm.

By "flake" is meant notably graphene, in particular with 1 to 10 layers, for example single layer, one or two of whose dimensions are less than or equal to 1 mm, in particular 500 μm, 100 μm or 10 μm.

According to a particular embodiment, said sets A, B and C of carbon atoms in the $sp^2$ hybridisation state are of the same nature, in particular graphene, more particularly in the form of sheet or flakes.

According to a particular embodiment:

- the set B of carbon atoms in the $sp^2$ hybridisation state is graphene in sheet form, and/or
- the set C of carbon atoms in the $sp^2$ hybridisation state is graphene in the form of flakes.

According to a particular embodiment, the invention relates to a biosensor comprising:

a first set A of carbon atoms in the $sp^2$ hybridisation state, said set being in contact with:

a plurality of compounds of the following formula ($I_1$):

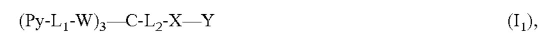

$$(Py-L_1-W)_3—C-L_2-X—Y \quad (I_1),$$

and optionally, a plurality of compounds of the following formula ($II_1$):

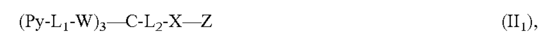

$$(Py-L_1-W)_3—C-L_2-X—Z \quad (II_1),$$

a second set B of carbon atoms in the $sp^2$ hybridisation state, said set being in contact with:

a plurality of compounds of the following formula ($I_2$):

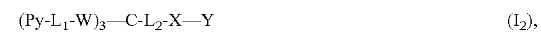

$$(Py-L_1-W)_3—C-L_2-X—Y \quad (I_2),$$

and a plurality of compounds of the following formula ($II_2$):

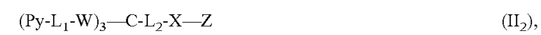

$$(Py-L_1-W)_3—C-L_2-X—Z \quad (II_2),$$

at least one third set C of carbon atoms in the $sp^2$ hybridisation state, said set being in contact with:

a plurality of compounds of the following formula ($I_3$):

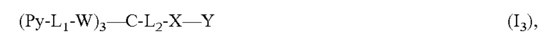

$$(Py-L_1-W)_3—C-L_2-X—Y \quad (I_3),$$

and a plurality of compounds of the following formula ($II_3$):

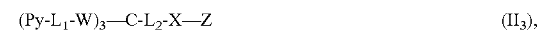

$$(Py-L_1-W)_3—C-L_2-X—Z \quad (II_3),$$

with, independently of the carbon set A to C and of the compound of the formula (I) to (II):

Py is a pyrenyl group;

$L_1$ is a C1-C12 alkanediyl group;

W represents a single bond, an arenediyl group, a heteroarenediyl group or a —O—$Ar_1$— group where $Ar_1$ is an arene or a heteroarene;

$L_2$ is a group of formula (A) as follows, $-(L_{2a})_i-(L_{2b})_j-$ wherein:

- i and j are independently of each other selected from 0 and 1, with i+j=1 or 2;
- $L_{2a}$ is a $C_1$-$C_{12}$ alkanediyl, $C_2$-$C_{12}$ alkenediyl or $C_2$-$C_{12}$ alkynediyl group;

$L_{2b}$ is an arenediyl group, a heteroarenediyl group or a group —O—$Ar_2$— where $Ar_2$ is an arene or a heteroarene;

X is —C(=O)N—, —C(=O)O— or —C(=O)S— group;

Y is an antibacterial antibody or a lectin;

Z is an antibacterial peptide;

and where the sets A, B and C are such that:

the set A is free of compounds of the formula ($II_1$) or the molar ratio of the amount of compounds of the formula ($II_1$) to that of compounds of the formula ($I_1$) is less than 0.1;

in the set B, the molar ratio of the amount of compounds of the formula ($I_2$) to that of compounds of the formula ($II_2$) being from 0.66 to 1.5, for example about 1.0; and in the set C, the molar ratio of the amount of compounds of the formula ($I_3$) to that of compounds of the formula ($II_3$) being from 0.33 to 0.66, for example about 0.5.

According to a particular embodiment, said set of carbon atoms in the sp2 hybridisation state is supported by a substrate, in particular selected from metals, metal oxides, glasses and polymers.

According to a particular embodiment, R, $L_1$, W, n, V, $L_2$, X, Y and Z are identical in the compounds of the formula (I) and (II), for the sets A, B and C.

According to a particular embodiment, R is the 1-pyrenyl or the 2-pyrenyl, in particular the 1-pyrenyl.

According to a particular embodiment, $L_1$ is a $C_2$-$C_8$ alkanediyl group, in particular the butanediyl.

According to a particular embodiment, W represents a —O—$Ar_1$— group where $Ar_1$ is an arene or a heteroarene, in particular a benzene, more particularly a para-substituted benzene.

According to a particular embodiment, i and j are both equal to 1.

According to a particular embodiment, $L_{2a}$ is a $C_2$-$C_{12}$ alkynediyl group, in particular —C≡C—.

According to a particular embodiment, $L_{2b}$ is an arenediyl group, in particular a benzenediyl, more particularly a para-substituted benzenediyl.

According to a particular embodiment, R, $L_1$, W, V, $L_2$ are as defined by the following formula:

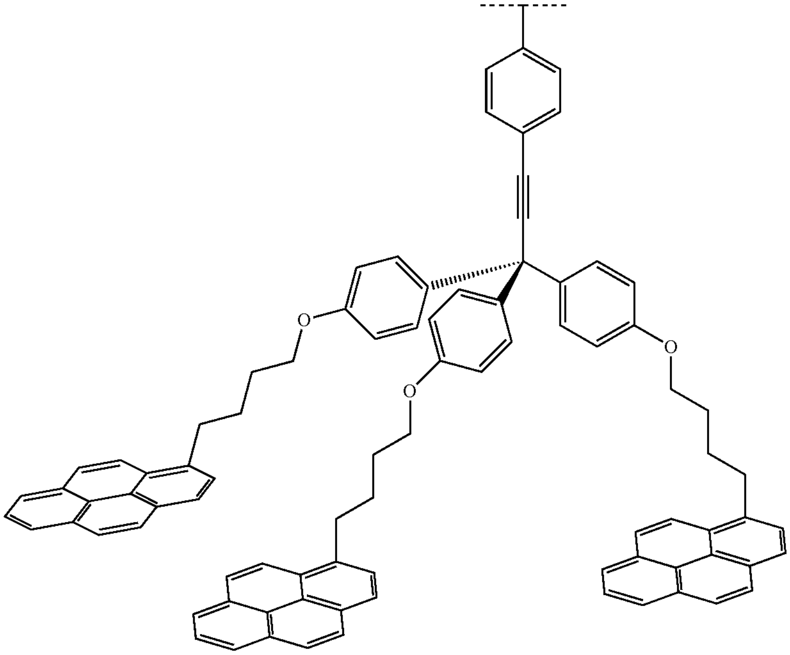

According to a particular embodiment, Y is selected from the antibodies against gram-positive bacteria, the antibodies against gram-negative bacteria, in particular the antibodies directed against one or more natural environmental and/or industrial effluent bacteria, the antibodies being more particularly antibodies against *Escherichia coli*, or in particular the antibodies directed against one or more luminescent bacteria, more particularly *Vibrio fischeri, Vibrio harveyi, Photobacterium phosphoreum, Shewanella hanedai, Shewanella woodyi*, and *Photorhabdus luminescens*.

The antibodies against *Escherichia coli* are well known to the person skilled in the art. For example, polyclonal antibodies, in particular from goat or from rabbit, in particular those recognizing numerous antigenic "O" and "K" serotypes of *Escherichia coli*, in particular those marketed by LifeSpan BioSciences (e.g. under the reference LS-C58854) or by Abcam (e.g. under the reference ab137967).

The antibodies may also be antibodies against *Escherichia coli*, preferably monoclonal, in particular from mice, specifically directed against particular strains of *E. coli*, for example particularly pathogenic strains such as the strain O157. This is in particular the case for the antibodies against *E Coli* O157 marketed by MyBioSource (for example under the reference MBS568193).

The antibodies against gram-positive bacteria and the antibodies against gram-negative bacteria are also well known to the person skilled in the art. These may include monoclonal antibodies directed against the endotoxins of the Gram-negative bacteria, in particular those marketed by ThermoFisher Scientific (for example under the reference MA1-10685).

According to a particular embodiment, Y is selected from the antibodies to directed against one or more environmental and/or industrial effluent bacteria.

These may be freshwater bacteria, including bacteria of the genus *Aeromonas*, for example *A. hydrophila*. For example, Y is an antibody against *A. hydrophila* (Aquac. Res. 48 2055-63).

They can be marine bacteria, in particular *Photobacterium phosphoreum* bacteria (Loic Recoules. Biocapteur pour la surveillance de la qualité de l'eau: Application aux eaux pluviales et de stations d'épurations. Micro et nanotechnologies/Microelectronique. Université Paul Sabatier-Toulouse III, 2015), or Aliivibrio *fischeri* bacteria (also referred to as *Vibrio fischeri*) (ibid.). Thus, Y is for example an antibody against *P. phosphoreum* or against *V. fischeri* (see e.g. ISO 11348 standardised Microtox test, 2009), in particular a horseradish peroxidase labelled anti-*vibrio* rabbit polyclonal antibody (Laczka O F et al., PLoS ONE 9(10), e108387).

Freshwater, marine and/or wastewater bacteria can also be *Escherichia coli* bacteria (Loic Recoules, ibid.), for example *Escherichia coli* bacteria carrying the IuxCDABE gene (from *A. fisheri*). Thus, Y is for example an antibody against *E. coli*, e.g. an unconjugated rabbit polyclonal anti-*E. coli* antibody (Jõgi E, Int. J. Environ. Anal. Chem. 1-12).

According to a particular embodiment, Y is selected from the antibodies directed against one or more luminescent bacteria, more particularly *Vibrio fischeri, Vibrio harveyi, Photobacterium phosphoreum, Shewanella hanedai, Shewanella woodyi*, and *Photorhabdus luminescens.*

According to a particular embodiment, Y is selected from the lectins, in particular those binding to sugars of the bacterial walls, more particularly the sugars present on the wall of the Gram-positive bacteria.

According to a particular embodiment, Y is the concanavalin A. This compound is in particular marketed by Sigma-Aldrich (for example under the reference C5275).

According to a particular embodiment, Z is selected from the cecropins, the defensins, the magainins and the dermaseptins, Z being in particular a cecropin.

According to a more particular embodiment, Z is selected from the cecropins, in particular cecropin A (SEQ ID NO:1), cecropin B (SEQ ID NO:2), cecropin P1 (SEQ ID NO:3), cecropin 1 (SEQ ID NO:4) and *Bombyx mori* cecropin (SEQ ID NO:5), defensins, in particular the defensin 6 (SEQ ID NO:6) and the defensin 5 (SEQ ID NO:7), the magainins, in particular the magainin B2 (SEQ ID NO:8) and the magainin R2 (SEQ ID NO:9) and the dermaseptins, in particular the dermaseptin H3 (SEQ ID NO:10) and the dermaseptin S1 (SEQ ID NO:11).

The cecropins A, B and P1 are in particular marketed by Sigma Aldrich.

According to a particular embodiment, the density of compounds of the formulae (I) and (II) on the surface of the set of carbon atoms in the $sp^2$ hybridisation state is comprised from about 1 of these compounds per 300 nm2 area to about 1 of these compounds per 2 nm2 area, in particular about 1 compound per about 2.7 $nm^2$ area.

According to a particular embodiment, the invention relates to a biosensor as defined above for determining the toxicity of substances present in an aqueous medium.

According to another aspect, the invention also relates to a method for preparing a biosensor as defined above, comprising the following steps:

(i) Contacting a first, a second, and at least a third set of carbon atoms in the $sp^2$ hybridisation state with a compound of the following formula (III)

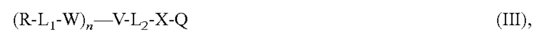

$$(R\text{-}L_1\text{-}W)_n\text{—}V\text{-}L_2\text{-}X\text{-}Q \qquad (III),$$

wherein:

R, $L_1$, W, V and $L_2$ are as defined above;

X-Q is a group selected from —C(═O)O—N-succinimidyl, —C(═O)-halide, in particular —C(═O)—Cl, —C(═O)—$N_3$, —C(═O)—O—N-imidazolyl, —C(═O)—O—C(═O)—R', with R' being a linear, branched or cyclic $C_1$-$C_{12}$ alkyl, —C(═O)—O-catecholborane, —C(═O)—O-benzotriazole, in particular —C(═O)O—N-succinimidyl, to obtain at least three sets of carbon atoms in the activated $sp^2$ hybridisation state;

(ii) Contact:

of the first set of carbon atoms in the activated $sp^2$ hybridisation state as obtained in the previous step with a first composition comprising an antibacterial antibody or a lectin and optionally an antibacterial peptide, to obtain a first functionalized set A of carbon atoms in the $sp^2$ hybridisation state;

of the second set of carbon atoms in the activated $sp^2$ hybridisation state as obtained in the previous step with a second composition comprising an antibacterial antibody or a lectin and an antibacterial peptide, to obtain a second functionalized set B of carbon atoms in the $sp^2$ hybridisation state;

of the third set of carbon atoms in the activated $sp^2$ hybridisation state as obtained in the previous step with a third composition comprising an antibacterial antibody or a lectin and an antibacterial peptide, to obtain a first functionalized set C of carbon atoms in the $sp^2$ hybridisation state.

Alternatively, the contacting of the step (ii) may be sequential, i.e. comprising a first contacting with a composition comprising an antibacterial antibody or a lectin and then a second contacting with a composition comprising an antibacterial peptide, or a first contacting with a composition comprising an antibacterial peptide and then a second contacting with a composition comprising an antibacterial antibody or a lectin.

All the embodiments defined above for the (functionalized) $sp^2$ hybridisation state biosensor also apply here, alone or in combination.

According to a particular embodiment, the contacting in the step (i) is carried out using a solution of the compound of the formula (III) in a solvent.

According to a more particular embodiment, said solvent is selected from the aprotic apolar solvents, in particular tetrahydrofuran, n-hexane, cyclohexane, 1,4-dioxane, toluene, diethyl ether, ethyl acetate, dichloromethane, in particular tetrahydrofuran.

According to a more particular embodiment, the compound of the formula (III) is present in the solution at a concentration comprised from 1 nM to 100 μM, for example at about 1 μM.

According to a particular embodiment, the contacting in the step (i) is done for a period of time from 10 seconds to 300 seconds, for example about 60 seconds.

According to a particular embodiment, the step (i) is followed, prior to the step (ii) by a step of washing the set of carbon atoms in the activated $sp^2$ hybridisation state, in particular with water.

According to a particular embodiment, the contacting in the step (ii) is carried out using a solution of the antibacterial antibody or of the lectin and the antibacterial peptide in a solvent.

According to a more particular embodiment, said solvent is selected from the phosphate buffered saline solutions, in particular the PBS 1×.

In a more particular embodiment, the antibacterial antibody or the lectin and the antibacterial peptide are present in the solution at a total concentration comprised from 10 μM to 10 μM, for example at about 10 nM.

According to a particular embodiment, the contacting in the step (ii) is carried out for a period of 10 minutes to 100 minutes, for example about 30 minutes.

According to a particular embodiment, step (ii) is followed by a step of washing the functionalized set of carbon atoms in the $sp^2$ hybridisation state, in particular with a phosphate buffered saline solution, in particular 1×PBS.

According to a particular embodiment, said sets of carbon atoms in the $sp^2$ hybridisation state are supported, independently or not, by a substrate, in particular selected from metals, metal oxides, glasses and polymers.

According to a particular embodiment, said sets of carbon atoms in the $sp^2$ hybridisation state are formed on the surface of said support, prior to step (i).

According to another particular embodiment, said sets of carbon atoms in the $sp^2$ hybridisation state are formed, as in particular well known to the person skilled in the art, and then transferred onto the surface of said support, prior to step (i).

For example, in the case of graphene, during a wet transfer, the copper layer used to grow the graphene can be dissolved on the surface of a copper etching bath (liquid) and the graphene is then brought into contact with the surface of said support.

Also as an example for the graphene, during a dry transfer, the graphene can in particular be detached from the copper growth substrate by adding a polymer (e.g. the parylene PDMS), then the polymer+graphene set is applied to the desired surface by mechanical action (mechanical peeling). The polymer is then removed.

According to another aspect, the invention also relates to the use of a biosensor as defined above for the determination of the toxicity of substances present in an aqueous medium.

All of the embodiments defined above in relation to the biosensor comprising the (functionalized) sets A, B and C of carbon atoms in the $sp^2$ hybridisation state also apply here, alone or in combination.

According to another aspect, the invention also relates to a method for determining the toxicity of substances present in an aqueous medium, comprising the following steps:

a) Contacting the sets A, B and C of carbon atoms in the $sp^2$ hybridisation state of the biosensor as defined above, with bacteria capable of being recognised by the antibacterial antibodies Y or of interacting with the lectins Y of said sets to obtain sets on which said bacteria are immobilised;
b) Contacting the sets as obtained in step a) with said aqueous medium;
c) Assessing the viability of said bacteria on the sets as obtained in step b).

According to a particular embodiment, said method is an in situ method.

According to a particular embodiment, the aqueous medium is a natural aquatic environment, in particular an aquatic environment consisting of or comprising fresh water, preferably selected from a river, a lake, a river and a canal.

In a particular embodiment, the aqueous medium is an industrial effluent.

The contacting according to step b) can be done, for example, by placing the sets as obtained in step a) in an enclosure which communicates with the outside environment, in particular via a filtering membrane. This filtering membrane has, for example, pore sizes ranging from 0.1 μm to 0.5 μm.

In a particular embodiment, the contacting in step b) is carried out for a period of time of between 1 and 20 minutes, for example about 15 minutes. This time is likely to allow the diffusion into the aqueous medium in contact with said sets as obtained in step a). In the example given in the previous paragraph, this time is likely to allow the diffusion to take place and the concentrations to be the same on both sides of the membrane. Optionally, a fluidic circulation system can be used to force the diffusion to take place more rapidly.

In a particular embodiment, the assessment according to step c) is repeated.

In a more particular embodiment, the assessment according to step c) is repeated so that the time between two successive assessments is between 1 minute and 30 minutes, for example about 15 minutes.

According to a particular embodiment, the total contact time between the aqueous medium and the sets as obtained in step a), corresponding in particular to the total time of step b) and step or steps c), is at most 2 to 48 hours, in particular at most 15 to 24 hours.

According to a particular embodiment, the assessment according to step c) is done by measuring the mass of said bacteria. This measurement is then made for each of the sets A, B and C.

For example, a first assessment is carried out according to step c) and is a reference measurement. Step c) is repeated, in particular so that measurements are carried out approximately every 15 minutes. If, for example, the mass of bacteria on the set A increases, the mass of bacteria on the set B remains stable, and the mass of bacteria on the set C decreases slightly, it can be concluded that the aqueous medium under investigation is not polluted. On the contrary, if the mass of bacteria on the set A remains stable or decreases, the mass of bacteria on the set B decreases slightly or strongly, and the mass of bacteria on the set C decreases strongly, in particular until there are no more bacteria, it can be concluded that the aqueous medium is polluted. If the latter case is the one observed as early as the second measurement (the measurement following the reference measurement), it can be concluded in particular that it is an acute pollution. If the latter case is only observed after the second measurement (i.e. after more than 30 minutes after the reference measurement), it can be concluded in particular that it is a chronic pollution.

According to a particular embodiment, the substances are pollutants, in particular selected from chemical, physical or biological pollutants, the chemical pollutants being preferably selected from liquid hydrocarbons, detergents and/or surfactants, plasticizers, pesticides, eutrophying materials, heavy metals, drugs, cosmetics and industrial products;

the physical pollutants are preferably selected from heat, noise, radioactivity and light;

the biological pollutants are preferably selected from algal toxins, pathogens and parasites.

In a particular preferred embodiment, the substances are chemical pollutants.

In a particular embodiment, the aqueous medium contains one or more bacteria, and the groups Y are selected from the antibodies directed against that or those bacteria. Thus, in this particular embodiment, the groups Y are selected from antibodies directed against one or more bacteria likely to be contained in the aqueous medium for which the measurement of the presence of toxic substances is desired.

According to a particular embodiment, the groups Y are selected from the antibodies directed against one or more luminescent bacteria, the bacteria of step a) are said one or more luminescent bacteria, and the assessment of the viability of said bacteria according to step c) is carried out by irradiation with a UV lamp and then measurement of the fluorescence, in particular with a camera.

According to a particular embodiment, the assessment of the viability of the bacteria according to step c) is done by measuring the mass of said sets A, B and C.

In a particular embodiment, the assessment of the viability of the bacteria according to step c) is carried out using optomechanical sensors.

According to a more particular embodiment, the assessment of the viability of bacteria according to step c) is carried out using optomechanical sensors comprising a support, at least one waveguide, at least one optical resonator suspended from the support, said optical resonator being optically coupled to the waveguide, at least one mechanical resonator suspended from the support, said mechanical resonator and said optical resonator being coupled, said mechanical resonator being configured to vibrate in a bulk mode and comprising at least one face extending in the plane of the sensor and configured to receive molecules of said given species, at least said face comprising the set A, the set B, and the at least one set C respectively, said mechanical resonator having a small dimension in a direction normal to the plane of the sensor relative to the dimensions of said face.

In a particular embodiment, the assessment of the viability of the bacteria according to step c) is carried out using a quartz crystal microbalance.

For example, each set A, B and C can be deposited on a quartz crystal microbalance and the resonant frequency read at a determined time, for example every minute. An increase in resonance frequency corresponds to an increase in mass, and thus to a bacterial growth, and therefore to an environment likely to be favourable to the bacterial growth because it is free of pollutants. Furthermore, a stable frequency corresponds to a constant mass, i.e. the bacteria studied are neither growing nor decay, as the bacteria that die are replaced by new ones, for example. Finally, if the resonance frequency decreases, it very generally means that the mass of the set decreases, and therefore the bacteria die in the environment. This is likely to mean, particularly if it concerns the set A and possibly the set B, that there is a pollutant present.

Definitions

As used in this description, the term "about" refers to a range of values within ±10% of a specific value. For example, the term "about 20" comprises the values of 20±10%, i.e., the values of 18 to 22.

For the purposes of this description, the percentages refer to percentages by mass in relation to the total mass of the formulation, unless otherwise stated.

As understood here, the value ranges in the form of "x-y" or "from x to y" or "between x and y" include the bounds x and y as well as the integers between these bounds. For example, "1-5", or "from 1 to 5" or "between 1 and 5" refer to the integers 1, 2, 3, 4 and 5. The preferred embodiments include each individual integer in the value range, as well as any sub-combination of those integers. For example, the preferred values for "1-5" may comprise the integers 1, 2, 3, 4, 5, 1-2, 1-3, 1-4, 1-5, 2-3, 2-4, 2-5, etc.

As used herein, the term "alkyl" means a linear or branched chain alkyl group having the number of carbon atoms indicated before said term, in particular 1 to 8 carbon atoms, such as methyl, ethyl, propyl, isopropyl, butyl, isobutyl, sec-butyl, tert-butyl, pentyl, isoamyl, neopentyl, 1-ethylpropyl, 3-methylpentyl, 2,2-dimethylbutyl, 2,3-dimethylbutyl, hexyl, octyl, etc. Thus, an expression such as "$C_1$-$C_4$ alkyl" designates an alkyl radical containing from 1 to 4 carbon atoms. The same applies to the term "alkane".

As used herein, the term "arene" refers to a substituted or unsubstituted mono- or bicyclic aromatic hydrocarbon cyclic system having 6 to 10 carbon atoms in the cycle. The examples include the benzene and the naphthalene. The preferred arenes include the unsubstituted or substituted benzene and naphthalene. The definition of "arene" includes condensed cyclic systems, including, for example, the cyclic systems in which an aromatic cycle is condensed to a cycloalkyl cycle. The examples of such condensed cyclic systems comprise, for example, the indane, the indene and the tetrahydronaphthalene.

As used herein, the term "heteroarene" refers to an aromatic cyclic system containing 5 to 10 carbon atoms in which one or more carbon atoms of the cycle are replaced by at least one heteroatom such as —O—, —N— or —S—. The examples of heteroarenes comprise pyrrole, furan, thiophene, pyrazole, imidazole, thiazole, isothiazole, isoxazole, oxazole, oxathiol, oxadiazole, triazole, oxatriazole, furazane, tetrazole, pyridine, pyrazine, pyrimidine, pyridazine, triazine, indole, isoindole, indazole, benzofuran, isobenzofuran, purine, quinazoline, quinoline, isoquinoline, benzoimidazole, benzothiazole, benzothiophene, thianaphthene, benzoxazole, benzisoxazole, cinnoline, phthalazine, naphthyridine and quinoxaline. The definition of "heteroarene" includes the condensed cyclic systems, comprising, for example, the cyclic systems in which an aromatic cycle is condensed to a heterocycloalkyl cycle. The examples of such condensed cyclic systems comprise, for example, phthalamide, phthalic anhydride, indoline, isoindoline, tetrahydroisoquinoline, chroman, isochroman, chromen and isochromene. [Table 1]

TABLE 1

| | |
|---|---|
| SEQ ID NO: 1 | Lys Trp Lys Leu Phe Lys Lys Ile Glu Lys Val Gly Gln Asn Ile Arg Asp Gly Ile Ile Lys Ala Gly Pro Ala Val Ala Val Val Gly Gln Ala Thr Gln Ile Ala Lys |
| SEQ ID NO: 2 | Lys Trp Lys Val Phe Lys Lys Ile Glu Lys Met Gly Arg Asn Ile Arg Asn Gly Ile Val Lys Ala Gly Pro Ala Ile Ala Val Leu Gly Glu Ala Lys Ala Leu |

TABLE 1-continued

| | |
|---|---|
| SEQ ID NO: 3 | Ser Trp Leu Ser Lys Thr Ala Lys Lys Leu Glu Asn Ser Ala Lys Lys rg Ile Ser Glu Gly Ile Ala Ile Ala Ile Gln Gly Gly Pro Arg |
| SEQ ID NO: 4 | Met Asn Phe Asn Lys Val Phe Ile Leu Val Ala Ile Val Ile Ala Ile Phe Ala Gly Gln Thr Glu Ala Gly Trp Leu Lys Lys Ile Gly Lys Lys Ile Glu Arg Val Gly Gln His Thr Arg Asp Ala Thr Ile Gln Thr Ile Ala Val Ala Gln Gln Ala Ala Asn Val Ala Ala Thr Ala Arg Gly |
| SEQ ID NO: 5 | Arg Trp Lys Ile Phe Lys Lys Ile Glu Lys Val Gly Gln Asn Ile Arg Asp Gly Ile Val Lys Ala Gly Pro Ala Val Ala Val Val Gly Gln Ala Ala Thr Ile |
| SEQ ID NO: 6 | Met Arg Thr Leu Thr Ile Leu Thr Ala Val Leu Leu Val Ala Leu Gln Ala Lys Ala Glu Pro Leu Gln Ala Glu Asp Asp Pro Leu Gln Ala Lys Ala Tyr Glu Ala Asp Ala Gln Glu Gln Arg Gly Ala Asn Asp Gln Asp Phe Ala Val Ser Phe Ala Glu Asp Ala Ser Ser Ser Leu Arg Ala Leu Gly Ser Thr Arg Ala Phe Thr Cys His Cys Arg Arg Ser Cys Tyr Ser Thr Glu Tyr Ser Tyr Gly Thr Cys Thr Val Met Gly Ile Asn His Arg Phe Cys Cys Leu |
| SEQ ID NO: 7 | Met Arg Thr Ile Ala Ile Leu Ala Ala Ile Leu Leu Val Ala Leu Gln Ala Gln Ala Glu Ser Leu Gln Glu Arg Ala Asp Glu Ala Thr Thr Gln Lys Gln Ser Gly Glu Asp Asn Gln Asp Leu Ala Ile Ser Phe Ala Gly Asn Gly Leu Ser Ala Leu Arg Thr Ser Gly Ser Gln Ala Arg Ala Thr Cys Tyr Cys Arg Thr Gly Arg Cys Ala Thr Arg Glu Ser Leu Ser Gly Val Cys Glu Ile Ser Gly Arg Leu Tyr Arg Leu Cys Cys Arg |
| SEQ ID NO: 8 | Gly Ile Gly Lys Phe Leu His Ser Ala Gly Lys Phe Gly Lys Ala Phe Leu Gly Glu Val Met Lys Ser |
| SEQ ID NO: 9 | Gly Ile Lys Glu Phe Ala His Ser Leu Gly Lys Phe Gly Lys Ala Phe Val Gly Gly Ile Leu Asn Gln |
| SEQ ID NO: 10 | Met Ala Phe Leu Lys Lys Ser Leu Phe Leu Val Leu Phe Leu Gly Met Val Ser Leu Ser Ile Cys Glu Glu Glu Lys Arg Glu Asn Glu Asp Glu Glu Leu Gln Glu Asp Asp Glu Gln Ser Glu Met Lys Arg Gly Leu Trp Ser Thr Ile Lys Asn Val Gly Lys Glu Ala Ala Ile Ala Ala Gly Lys Ala Ala Leu Gly Ala Leu |
| SEQ ID NO: 11 | Met Asp Ile Leu Lys Lys Ser Leu Phe Leu Val Leu Phe Leu Gly Leu Val Ser Leu Ser Ile Cys Glu Glu Glu Lys Arg Glu Asn Glu Asp Glu Glu Lys Gln Glu Asp Asp Glu Gln Ser Glu Met Lys Arg Ala Leu Trp Lys Thr Met Leu Lys Lys Leu Gly Thr Met Ala Leu His Ala Gly Lys Ala Ala Leu Gly Ala Ala Ala Asp Thr Ile Ser Gln Gly Thr Gln |

FIGURES

FIG. 1 shows a protocol for the manufacture of the biosensors according to example 1. Legend: Oxyde=Oxide, Disque=Disk, Entree=Entrance, Sortie=Exit, Oxyde de $SiH_4$=Oxide of $SiH_4$.

The steps illustrated are as follows:

1. Thinning of the upper Si layer
2. Thermal oxidation
3. Alignment markings for lithography
4. Manufacturing of the optical network (input and output)
5. Manufacturing of the optical guides, micro discs and electrodes.
   a) Chemical vapour deposition at low pressure and creation of a silane oxide ($SiH_4$) hard mask at high temperature
   b) Lithography of the upper Si layer and removal of residues
   c) Removal of the $SiH_4$ and the native oxides
6. Manufacturing of the AlSi electrodes
   a) Second thermal oxidation
   b) Localized doping of Si
   c) Chemical vapour deposition of $SiH_4$ oxide, levelling and modelling ($SiH_4$ oxide)
   d) Vapour deposition of AlSi
   e) Chemical-mechanical levelling of AlSi
7. Forming the pedestal of the micro disc
   a) Hydrofluoric acid vapour etching of the $SiH_4$ layers and of the native oxides
   b) Hydrofluoric acid vapour etching of the oxide layer (BOX).

EXAMPLES

Example 1: Manufacturing of Optomechanical Biosensors with Functionalized Graphene According to the Invention The manufacture of these functionalized graphene biosensors is carried out in 3 steps.

1. Manufacturing of the Biosensors

A fabrication protocol for the biosensors is presented in FIG. 1 (Microdisques optomécaniques résonants en silicium pour la detection biologique en milieu liquide, thesis by Maxime HERMOUET defended on 26 Mar. 2019, Communauté Université Grenoble Alpes).

2. Manufacturing and Deposition of Graphene on the Biosensor Micro Discs

The manufacture and the deposition of graphene is generally performed as follows. This deposition is generally performed between steps 7a) and 7b) as described in FIG. 1.

The protocol is presented below (for example online with Courtin Jules.

Hétérostructure graphéne/silicium: de la formation de l'interface aux propriétés de transport électronique. Physique. Université Rennes 1, 2020):

1. The graphene manufacture can be made by a chemical deposition in vapor phase from a mixture of gases, at least one of which is carbon, which is heated up to the obtention of a plasma. This plasma then allows the deposition of a graphene layer on copper
2. The graphene is then covered by spin-coating with a PMMA (PolyMethylMethacrylAte) film
3. The copper is then etched with a 9% $FeCl_3$ solution
4. Successive baths of deionised water and 12% HCl allow to reduce the pollution induced by the $FeCl_3$ bath
5. The PMMA/graphene stack is then transferred to the silicon surface of the micro disc of the biosensor
6. Acetone and isopropranolol baths for 1 hour at room temperature allow to remove a maximum of PMMA residues.
7. Optionally, a photosensitive resin coating/photolithography/or RIE etching step allow to remove the graphene from undesired areas (i.e. outside of discs)

3. Functionalization of the Graphene Layers

The functionalization is carried out by grafting the tripod of the invention onto the graphene monolayer, followed by treatment with antibodies and/or antimicrobial peptide, as defined above, and as follows:

Surface Suitable for the Bacterial Growth—Set A

A molar ratio antimicrobial peptide/antibody of less than 0.1, for example 100% antibody Bacteriostatic Surface—Set B A molar ratio antibody/antimicrobial peptide in the range of 0.66 to 1.5, for example:

50% molar antibody

50% molar antimicrobial peptide

Bactericidal Surface—Set C

A molar ratio antibody/antimicrobial peptide in the range of 0.33 to 0.66, for example:

25% molar antibody

75% molar of antimicrobial peptide

Example 2: Use of the Biosensors

Optional Test Phase:

In order to verify the survival of the bacteria under the desired stress conditions, the developed biosensors are tested in increasingly complex matrices as follows.

For this purpose, the following solutions are injected into the microfluidic system of the biosensor in example 1:

1) biological/physiological buffer solution used in microbiology (Ringer, Phosphate-Buffered Saline (PBS));
2) natural filtered water (freshwater or marine);
3) unfiltered natural waters (freshwater or marine);
4) and wastewater.

Actual Use:

The bacteria used in the biosensors are chosen in particular according to the choice of the freshwater/marine/wastewater studied.

The survival of the bacteria can be identified through the images obtained by the camera, for the bioluminescent bacteria, and/or through the variability of the optical and electrical signals (MEMS-OMNR: micro electromechanical system-optomechanical nanoresonator).

The time it takes to observe the start of bacterial decay with the buffer solutions provides information on the "validity period" of the sensors.

The observable results (e.g. viable bacteria, viable but not growing bacteria, non-viable bacteria) under the stress conditions shown below:

minimum stress:surface 100% antibodies/0% antimicrobial peptides;

bacteriostatic conditions: 50% antibodies/50% antimicrobial peptides;

bactericidal conditions (very high to maximum stress): 25% antibodies/75% antimicrobial peptides.

allow an eco-toxicological assessment of the risks. For example, the more the waters analysed have the capacity to impact the bacteria under negligible levels of stress, the more the ecotoxicological risks can be considered non-negligible.

Usage Details of the Sensor:

The sensor is installed in the aqueous medium to be measured, with the system partially or fully immersed.

The various sets of the sensor or sensors are installed in an enclosure that communicates with the outside environment via a filtering membrane (pore size between 0.1 μm and 0.5 μm) and are left for a few minutes until the diffusion takes place and the concentrations are identical on each side of the membrane. Optionally, a fluidic circulation system can be used to force the diffusion to take place more quickly.

A $1^{st}$ measurement of each of the sets is taken, which corresponds to a reference measurement.

Then, new measurements are taken every 15 minutes.

Two Cases can be Distinguished:

Case 1: no pollution in the environment: the mass of bacteria on set A increases, the mass of bacteria on B remains stable and on C decreases slightly (bactericidal surface so the bacteria will generally die).

Case 2: Pollution: the mass on A remains stable or decreases, on B decreases slightly or strongly and on C decreases strongly until there are no more bacteria.

If the case 2 is observed as early as the $2^{nd}$ measurement (15 minutes after equilibrium), it is generally an acute pollution.

If the case 2 is only observed after more than 30 minutes, it is generally a case of chronic pollution.

The invention claimed is:

1. A biosensor comprising:

a first set A of carbon atoms in the $sp^2$ hybridisation state, said set being in contact with:

a plurality of compounds of the following formula (11):

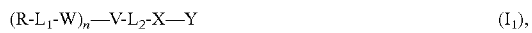

$(R-L_1-W)_n—V-L_2-X—Y$ $(I_1)$, and optionally, a plurality of compounds of the following formula (III):

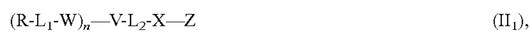

$(R-L_1-W)_n—V-L_2-X—Z$ $(II_1)$, a second set B of carbon atoms in the $sp^2$ hybridisation state, said set being in contact with:

a plurality of compounds of the following formula $(I_2)$:

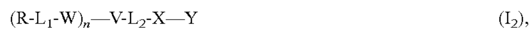

$(R-L_1-W)_n—V-L_2-X—Y$ $(I_2)$, and a plurality of compounds of the following formula $(II_2)$:

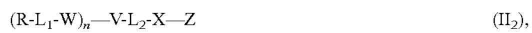

$(R-L_1-W)_n—V-L_2-X—Z$ $(II_2)$, a third set C of carbon atoms in the $sp^2$ hybridisation state, said set being in contact with:

a plurality of compounds of the following formula $(I_3)$:

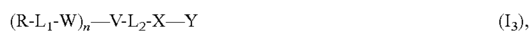

$(R-L_1-W)_n—V-L_2-X—Y$ $(I_3)$, and a plurality of compounds of the following formula $(II_3)$:

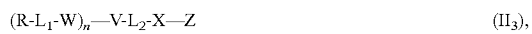

$(R-L_1-W)_n—V-L_2-X—Z$ $(II_3)$, with, independently of the carbon set A to C and of the compound of the formula (I) to (II):

n is equal to 1, 2, or 3;

V represents, for all n, $—C(H)_{3-n}—$ or:

when n is equal to 2, —C(H)═, C being in this case bonded to $L_2$ by a double bond;

when n is equal to 1, —C≡, C being in this case bonded to $L_2$ by a triple bond;

R is an aromatic hydrocarbon comprising from 2 to 6 condensed aromatic cycles;

$L_1$ is a $C_1$-$C_{12}$ alkanediyl group;

W represents a single bond, an arenediyl group, a heteroarenediyl group or a $—O—Ar_1—$ group where $Ar_1$ is an arene or a heteroarene;

$L_2$ is a group of formula (A) as follows, $-(L_{2a})_i-(L_{2b})_j-$ wherein:

i and j are independently of each other selected from 0 and 1, with i+j=1 or 2;

$L_{2a}$ is a $C_1$-$C_{12}$ alkanediyl, $C_2$-$C_{12}$ alkenediyl or $C_2$-$C_{12}$ alkynediyl group;

$L_{2b}$ is an arenediyl group, a heteroarenediyl group or a group $—O—Ar_2—$ where $Ar_2$ is an arene or a heteroarene;

X is a —C(═O)N—, —C(═O)O— or —C(═O)S— group;

Y is an antibacterial antibody or a lectin;

Z is an antibacterial peptide;

and where the sets A, B and Care such that:

the set A is free of compounds of the formula $(II_1)$ or the molar ratio of the amount of compounds of the formula $(II_1)$ to that of compounds of the formula $(I_1)$ is less than 0.1;

in the set B, the molar ratio of the amount of compounds of the formula $(I_2)$ to that of compounds of the formula $(II_2)$ being from 2:3 to 3:2; and in the set C, the molar ratio of the amount of compounds of the formula $(I_3)$ to that of compounds of the formula $(II_3)$ being from 1:3 to 2:3.

2. The biosensor of claim 1, comprising:

at least two sets B of carbon atoms in the $sp^2$ hybridisation state, for which the molar ratio of the amount of compounds of the formula $(I_2)$ to that of compounds of the formula $(II_2)$, being from 2:3 to 3:2, differs; and/or at least two sets C of carbon atoms in the $sp^2$ hybridisation state, for which the molar ratio of the amount of compounds of the formula $(I_3)$ to that of compounds of the formula $(II_3)$, being from 1:3 to 2:3, differs.

3. The biosensor according to claim 1, wherein said sets A, B and C of carbon atoms in the $sp^2$ hybridisation state are independently selected from graphene, graphene oxide, graphite, carbon nanotubes, fullerenes and fullerites.

4. The biosensor according to claim 1, wherein R, $L_1$, W, n, V, $L_2$, X, Y and Z are the same in the compounds of the formula (I) and (II), for the sets A, B and C.

5. The biosensor according to claim 1, wherein:

R is a 1-pyrenyl or a 2-pyrenyl;

$L_1$ is a $C_2$-$C_8$ alkanediyl group;

W represents a group $—O—Ar_1—$ where $Ar_1$ is an arene or a heteroarene;

i and j are equal to 1;

$L_{2a}$ is a $C_2$-$C_{12}$ alkynediyl group;

$L_{2b}$ is an arenediyl group.

6. The biosensor according to claim 1, wherein:

Y is selected from antibodies against gram-positive bacteria and antibodies against gram-negative bacteria;

Z is selected from cecropins, defensins, magainins and dermaseptins.

7. The biosensor according to claim 1, wherein the density of compounds of the formulae (I) and (II) on the surface of the sets of carbon atoms in the $sp^2$ hybridisation state is from about 1 of such compounds per 300 $nm^2$ area to about 1 of such compounds per 2 $nm^2$ area.

8. The biosensor according to claim 1, wherein R, $L_1$, W, V and $L_2$ are collectively defined by the following formula:

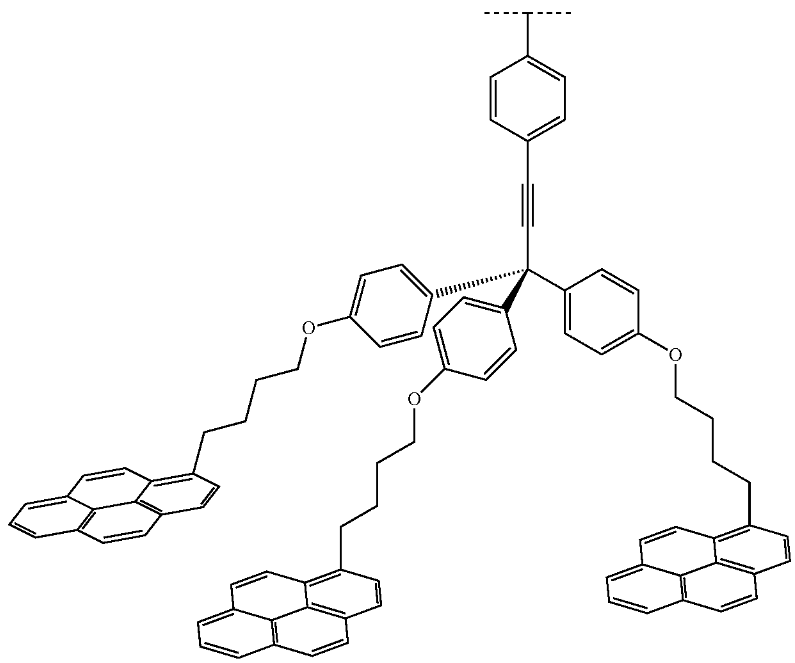

9. A method for the determination of the toxicity of substances present in aqueous medium comprising contacting the aqueous medium with the biosensor according to claim 1.

10. A method for determining the toxicity of substances present in an aqueous medium, comprising the following steps:

a) Contacting the sets A, B and C of carbon atoms in the $sp^2$ hybridisation state of the biosensor according to claim 1, with bacteria capable of being recognized by the antibacterial antibodies Y or of interacting with the lectins Y of said sets to obtain sets on which said bacteria are immobilized;

b) Contacting the sets as obtained in step a) with said aqueous medium;

c) Assessing the viability of said bacteria on the sets as obtained in step b).

11. The method according to claim 10, wherein:

the groups Y are selected from antibodies directed against one or more bacteria likely to be contained in the aqueous medium for which the measurement of the presence of toxic substances is desired; or the groups Y are selected from antibodies directed against one or more luminescent bacteria, the bacteria of step a) are said one or more luminescent bacteria, and the assessment of the viability of said bacteria according to step c) is carried out by irradiation with a UV lamp and then measurement of the fluorescence.

12. The method according to claim 10, wherein the assessment of the viability of the bacteria according to step c) is done by measuring the mass of said sets A, B and C.

* * * * *